United States Patent [19]

Nielsen

[11] 4,150,562
[45] Apr. 24, 1979

[54] METHOD AND MEANS FOR TEMPERATURE COMPENSATION IN EXHAUST GAS SENSORS

[75] Inventor: Arnold D. Nielsen, Wayne, Mich.

[73] Assignee: Ford Motor Company, Dearborn, Mich.

[21] Appl. No.: 911,257

[22] Filed: May 31, 1978

[51] Int. Cl.² .................................. G01N 27/46
[52] U.S. Cl. ........................ 73/27 R; 123/32 EA
[58] Field of Search ............... 73/27 R, 346; 123/32 EA; 60/285, 276

[56] References Cited

U.S. PATENT DOCUMENTS

| | | | |
|---|---|---|---|
| 3,868,846 | 3/1975 | Kushida et al. | 73/27 R |
| 3,915,135 | 10/1975 | Kushida et al. | 123/32 EA |
| 3,933,028 | 1/1976 | Laud et al. | 73/27 R |
| 3,946,198 | 3/1976 | Foote | 219/497 |
| 4,028,642 | 6/1977 | Kushida et al. | 323/75 B |

*Primary Examiner*—Anthony V. Ciarlante
*Attorney, Agent, or Firm*—Peter Abolins; Keith L. Zerschling

[57] ABSTRACT

This specification discloses an apparatus and method for sensing the composition of an engine exhaust gas wherein a signal for compensating for the temperature dependence of the apparatus is derived from engine speed. That is, the output of an exhaust gas sensor is measured with respect to a reference value which is a function of engine speed. The reference value includes the sum of a constant biasing voltage and a voltage representing engine speed.

15 Claims, 3 Drawing Figures

METHOD AND MEANS FOR TEMPERATURE COMPENSATION IN EXHAUST GAS SENSORS

BACKGROUND OF THE INVENTION

1. Field of the Invention

The present invention is directed to the field of electrochemical gas analyzers. More particularly, the present invention is directed to that portion of the above-noted field which is concerned with the generation of an electrical signal indicative of a gas chemistry. More specifically still, the present invention is directed to that portion of the above-noted field which is concerned with electrochemical gas sensors responsive to the partial pressure of oxygen in gaseous samples. More particularly still, the present invention is directed to that portion of the above-noted field which is concerned with the generation of an electrical signal indicative of the partial pressure of oxygen within the heated gaseous combustion by-products generated by an internal combustion engine. More particularly still, the present invention is directed to that portion of the above-noted field which is concerned with the generation of an electrical signal which may be rendered relatively insensitive to changes in the temperature of the gaseous combustion by-products while responding rapidly to variations in the partial pressure of oxygen in the gaseous combustion by-products.

2. Description of the Prior Art

It has been determined that the operation of a conventional automotive internal combustion engine produces gaseous combustion by-products including hydrocarbons, carbon monoxide and various oxides of nitrogen. Various efforts are being made to reduce the quantity of such by-products. Extensive investigation into the combustion process, examination of alternative combustion processes and detailed studies of exhaust gas treatment devices have lead to the conclusion that the use of a catalytic converter within the exhaust system of an internal combustion engine provides a practical and effective technique for substantially reducing the emission of the gaseous combustion by-products into the atmosphere. A catalytic exhaust treatment device or converter which is capable of substantially simultaneously converting all three of the aforementioned combustion by-products into water, carbon dioxide, and gaseous nitrogen is referred to as a "three-way catalyst." However, for the known three-way catalyst devices to be most effective, the gaseous by-products introduced into the converter must be the by-products of combustion of a substantially stoichiometric air/fuel mixture. Such three-way catalysts are said to have a very narrow "window" of air/fuel ratios at which the device is most efficiently operative on these three combustion by-products. By way of example if λ is the air/fuel ratio normalized to stoichiometry, the window may extend from about 0.99λ to about 1.01λ. Such a three-way catalyst converter is described, for example, in U.S. Pat. No. 3,895,093 issued to Weidenback et al. on July 15, 1975, assigned to KaliChemi Aktiengesellschaft and titled Catalytic Removal of Carbon Monoxide Unburned Hydrocarbons and Nitrogen Oxides From Automotive Exhaust Gas. For air/fuel ratios of the combustion mixture on either side of the window, one or two of the aforementioned combustion by-products will be converted in only very small percentages. Within the window, the three by-products will be converted at very high percent efficiencies approaching 90% in some cases. In view of the narrowness of the catalytic converter window, it has been determined that the associated internal combustion engine should be operated with a combustible mixture having an air/fuel ratio as close as possible to stoichiometry.

The most satisfactory technique for assuring continuous or substantially continuous operation at the desired air/fuel ratio is through the utilization of an appropriate feedback control mechanism. In implementing suitable feedback control systems, it has been proposed to employ sensors responsive to the chemistry of the exhaust gases, that is, the hot gaseous by-products of combustion, in order to control the precise air content and/or fuel content of the air/fuel mixture being provided to the engine.

One type of electrochemical exhaust gas sensor employs a ceramic material which demonstrates a predictable electrical resistance change when the partial pressure of the oxygen of its environment changes. An example of such a material is titania (titanium dioxide having a general formula $TiO_2$). Such sensors can be fabricated generally in accordance with the teachings of U.S. Pat. No. 3,886,785 issued to Stadler et al., titled Gas Sensor and Method of Manufacture and assigned to the assignee hereof. Tests of such devices have shown that at elevated and substantially constant temperatures, the devices will demonstrate a virtual step change in resistance for rich-to-lean and lean-to-rich excursions of the air/fuel ratio of the combustion mixture producing the exhaust gas environment of the device.

A principal difficulty which has been encountered with such variable resistive devices resides in the fact that such devices will demonstrate a measurable resistance change which is also a function of change of the temperature of the ceramic material, for example a change of about 500° F. produces a measurable resistance change on the order of magnitude of a sensed rich-to-lean or lean-to-rich air/fuel mixture change. Such a temperature variation can be encountered, depending of course to some extent on the location of placement of the sensor within an exhaust system, during acceleration of the associated engine from idle speed to highway speeds. Heretofore, exhaust gas sensors which employed a variable resistance sensor ceramic have required that the temperature of the material be relatively closely controlled for reliable use in a feedback system intended to provide an internal combustion engine with very precise air/fuel ratio control.

Temperature control of the associated sensor has required the addition of expensive electronic temperature sensing and heating control systems external to the exhaust conduit and the addition of a heater element per se situated internally of, or in close proximity to, the sensor element. In order to narrow the operational range of temperature of the sensor, the sensor has been operated at the higher end of the predictable range of exhaust gas temperatures thus requiring substantially continuous application of heat energy for most of the operating cycles of the associated engine. While such devices have continued to be of rugged construction, the addition of the heater and associated electronics devoted to temperature control have increased cost and have increased statistical failure problems. An additional problem which has been encountered is a ceramic fracture problem believed to be associated with thermal shock caused by the rapid heating of the ceramic material by the heater element. For less precise operation, such devices have been required to be installed at a location in an exhaust gas environment where the temperature of the exhaust gases will not vary substantially for variation in the operating cycle of the associated engine.

Since variable resistance exhaust gas sensor devices are of substantially greater mechanical strength and ruggedness than are other known types of exhaust gas sensor and are not subject to the temperature gradient which is inherent in operation of a galvanic cell type of exhaust gas sensor, it is an object of the present invention to provide a variable resistance exhaust gas sensor construction which is relatively temperature insensitive. With greater particularity, it is an object of the present invention to provide a titania exhaust gas sensor construction which is capable of producing an output signal which is rendered relatively insensitive to the temperature of the surrounding environment. With greater particularity still, it is a further and particular object of the present invention to provide a variable resistance ceramic exhaust gas sensor construction which is relatively insensitive to the temperature of the surrounding medium and which need not be maintained at a substantially constant temperature. With the foregoing objective in mind, it is a further object of the present invention to provide an exhaust gas sensor which does not require the application of external heating energy. It is also a further and particular objective of the present invention to provide a means of temperature compensation for a variable resistance ceramic exhaust gas sensor whereby sensor performance over a relatively wide range of operating temperatures will be relatively temperature insensitive. In furtherance of the foregoing objectives, it is a further and particular objective of the present invention to provide a variable resistance ceramic exhaust gas sensor with temperature compensation in the form of a high temperature thermistor in a construction which is rugged in use and which does not require expensive manufacturing techniques or equipment.

One attempt known in the prior art for satisfying the above requirements is to provide a pair of electrically series connected variable resistance ceramic sensor elements. One of the ceramic sensor elements is a variably resistive partial pressure of oxygen responsive and temperature responsive ceramic such as, for example, titania. The other of the ceramic sensor members is a variably resistive temperature responsive thermistor. The ceramic sensor members are connected electrically in series and are arranged to define a voltage divider network. When a reference voltage is applied across the voltage divider network, the voltage appearing at the junction between the ceramic sensor members may define the output voltage of the exhaust gas sensor construction. The voltage appearing at the junction of the sensor elements and the voltage divider network will be relatively temperature independent since temperature effects on the ceramic members will be electrically complementary. By comparing the output voltage to the voltage level at either end of the voltage divider network a useful output signal may be derived. By selectively referencing to define the output signal as either the voltage drop across the partial pressure of oxygen responsive member or the voltage drop across the thermistor sensor member, the resulting output signal can be rendered to be responsive to the air/fuel ratio. The use of two such elements in the exhaust gas sensor construction increases the statistical chances of failure. Further, it is desirable to obstruct the flow of exhaust gases as little as possible and the use of two such sensors obstructs it more than the use of a signal sensor.

SUMMARY OF THE INVENTION

This invention recognizes that a temperature compensated electrical sensor for determining the air/fuel ratio can be accomplished by electrically processing the output of a single sensor which is both responsive to changes in temperature as well as air/fuel ratio. More particularly, this invention recognizes that it is possible to compensate for the variation in a sensor's characteristics with temperature through use of a signal voltage related to engine speed. As a result, there is no need to provide a controlled power supply for a heater adjacent the gas sensor to make sure the gas sensor operates at a standard temperature. Further, there is no need to place a temperature sensor resistance in the exhaust stream, in addition to the gas sensor, to provide temperature compensation for the gas sensor.

In particular, this invention includes a gas sensor construction comprising a variably resistive gas and temperature sensing element adapted to be mounted in a gas stream for producing a first electrical signal responsive to the partial pressure of oxygen of the gas stream and to the temperature of the gas stream. A measuring means develops a second electrical signal as a function of engine speed. An electrical circuit means processes the electrical signals from the sensing element and the measuring means so that the second electrical signal is used to reduce the temperature dependency of the first electrical signal.

DETAILED DESCRIPTION OF THE PREFERRED EMBODIMENT

Figure 1:
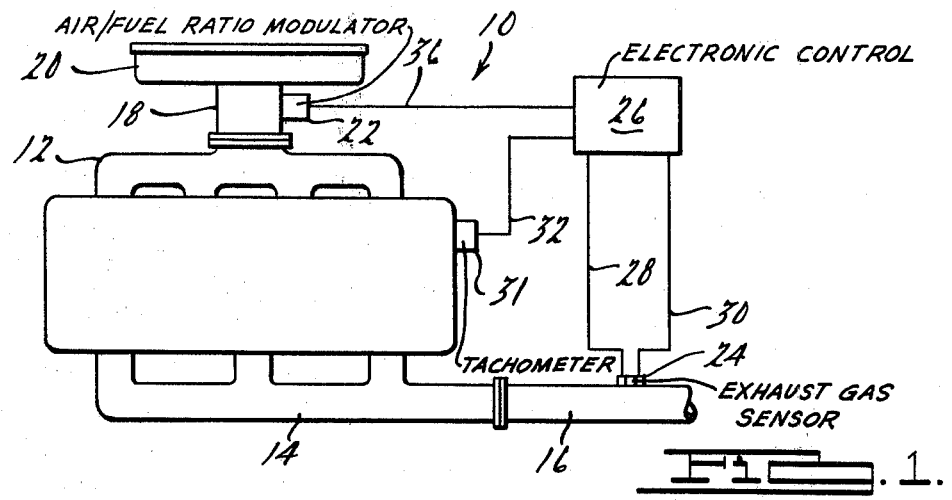
FIG. 1 is a schematic diagram illustrating an internal combustion engine having an exhaust responsive feedback fuel control mechanism in accordance with an embodiment of this invention.

Referring to FIG. 1, an internal combustion engine 10 includes an intake manifold 12 and an exhaust manifold 14. Exhaust manifold 14 communicates with an exhaust gas conduit 16. A fuel metering and delivery device 18, which may be for example, a fuel injection system or a carburetor, is illustrated schematically communicating with the intake manifold 12. Fuel metering and delivery device 18 is provided with an air cleaner 20 such that air injected by engine 10 through intake manifold 12 may be drawn from the atmosphere through air cleaner 20 and through at least a portion of the fuel metering and delivery device 18. Fuel metering and delivery device 18 is further provided with an air/fuel ratio modulator means 22. Air/fuel ratio modulator means 22 may be, for example, in case of an electronic fuel injection system, a variable resistor arranged to control the quantity of fuel delivered to engine 10 in relation to a given quantity of air or, in the case of a carburetor, may be a variably positioning metering orifice arranged to control the quantity of fuel delivered to engine 10 with respect to a given quantity of air. The air/fuel ratio modulator means 22 may alternatively be arranged to control a variable positionable air valve so that the quantity of air injected by engine 10 with respect to a given quantity of fuel delivered by fuel metering and delivery device 18 may be modulated.

Exhaust gas conduit 16 is provided with an exhaust gas sensor 24 which is mounted to conduit 16 so as to place an exhaust gas chemistry responsive element with the stream of exhaust gases flowing through conduit 16. A variety of forms of this device are suitable and include a variably resistive ceramic exhaust gas sensor form of, for example, titania or cobalt monoxide. Electronic control means 26 communicates with exhaust gas sensor 24 through sensing leads 28 and 30. Electronic control means also communicates with the air/fuel ratio modulator means 22 over a conductive lead 36. An engine tachometer 31 generates electrical voltage proportional to the engine speed or revolutions per minute of engine 10. Electronic control means 26 communicates with engine tachometer 31 over a conductive lead 32. As described hereinbelow, electronic control means 26 is arranged to respond to changes in the exhaust gas chemistry sensed by exhaust gas sensor 24 to provide a control signal for receipt by air/fuel ratio modulator means 22 which control signal may be arranged to modulate either the fuel or the air content of the air/fuel ratio mixture being provided to internal combustion engine 10 to maintain a desired exhaust gas chemistry. Additionally, electronic control means 26 compensates for changes in exhaust gas sensor 24 due to the temperature of the exhaust gas stream. An input from engine tachometer 31 is used to provide a temperature compensation which is based on the relationship between the temperature of the exhaust gas stream and the revolution per minute of the engine. That is, it can easily be appreciated that at very low revolutions of the engine the temperature is lower than at very high revolutions of the engine.

Figure 3:
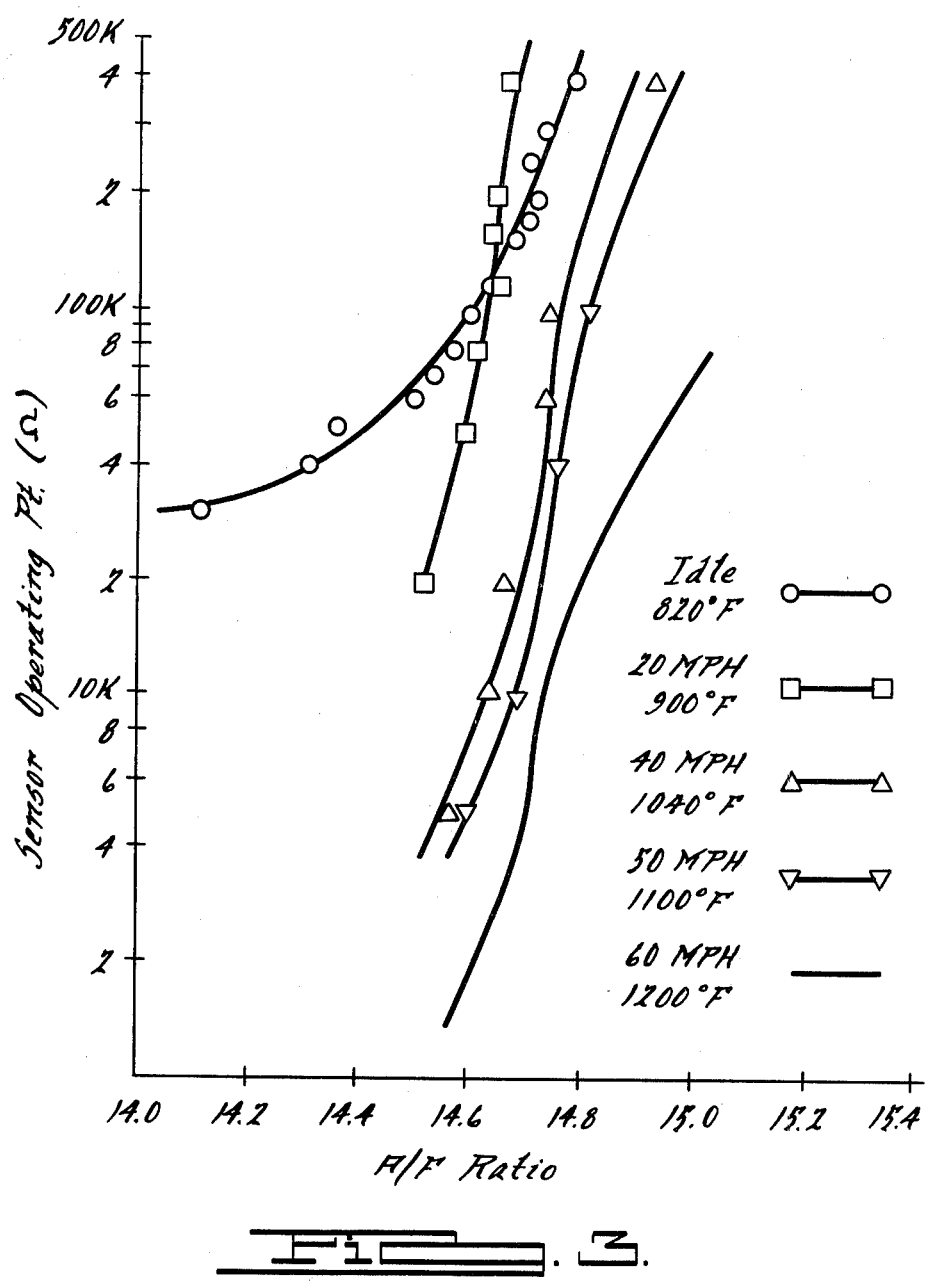
FIG. 3 is a graph of exhaust gas sensor resistance magnitude verses air to fuel ratio and the resultant shift in operating point due to speed changes from idle to 60 mph.

Without temperature compensation, the change in the resistance of the gas sensor, e.g., a $TiO_2$ material sensor, can be seen in FIG. 3. As shown in FIG. 3, the air to fuel ratio can shift as much as 0.46 from an idle condition to a 60 mph condition. In tabular form the change in voltage output from the gas sensor as measured at an interface circuit 40 described below is:

| Vehicle Speed M.P.H. | Temp. °F. | Operating Pt. of Sensor at Stochiometry | Interface Output |
|---|---|---|---|
| IDLE | 820 | 120K | .43V |
| 20 | 900 | 80K | .48V |
| 40 | 1040 | 8.5K | .9V |
| 50 | 1160 | 5K | .98V |
| 60 | 1280 | 2K | 1.08V |

Ideally it would be desirable to have the interface output remain constant as at stoichiometry even if there is variation in the temperature of the exhaust gas. This invention recognizes that such temperature compensation can take place using a parameter based upon engine speed.

Particular parameters which have been experimentally found indicate that the temperature correction is of the form $A(B+X)$ where A and B are constants and X is a function of engine speed. For example, when X is a voltage of the magnitude 0.123 volts/1000 rpm the correction can be 1.9 (0.105+X). Experimental data indicates that an assumption of a linear relationship between vehicle speed and exhaust temperature is justified.

Figure 2:
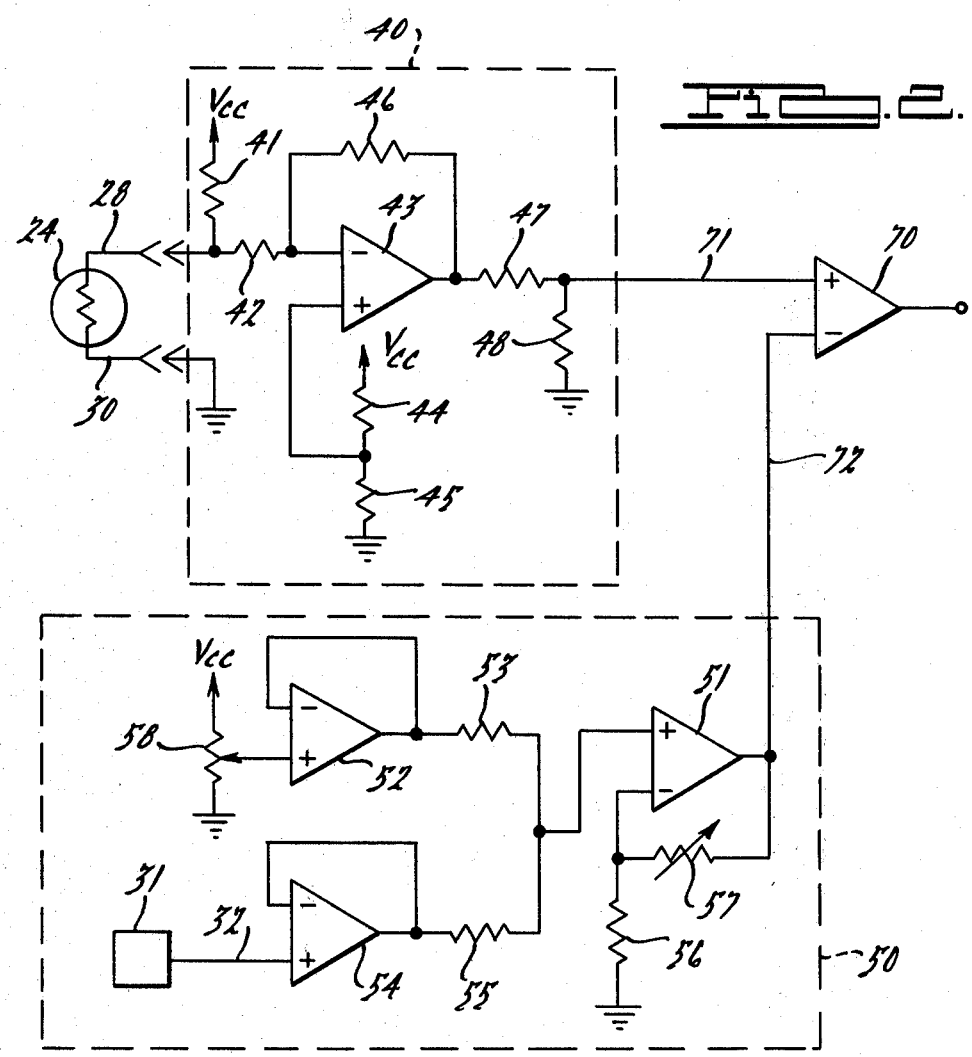
FIG. 2 is a circuit diagram, partly in block form, the electronic fuel control feedback and temperature compensation circuit in accordance with an embodiment of this invention.

Referring to FIG. 2, electronic control means 26 includes an interface 40 coupled to exhaust gas sensor 24 by sensing leads 28 and 30, and a compensation circuit 50 coupled to engine tachometer 31 by conductive lead 32. A comparator 70 has an output connected by conductive lead 36 to air/fuel ratio modulator means 22 which includes an interface such as a motor drive circuit utilizing an electrical signal carried by conductive lead 36 to adjust the air/fuel ratio. A first positive input of comparator 70 is connected by a conductive lead 71 to the output of interface circuit 40, and from a second negative input, by a conductive lead 72 to the output of compensation circuit 50.

Interface circuit 40 acts to convert exhaust gas sensor 24 resistance change to voltage change and includes a resistor 41 coupled between a voltage $V_c$ and sensing lead 28. Sensing lead 30 is coupled between exhaust gas sensor 24 and ground. Accordingly, resistor 41 and exhaust gas sensor 24 act in combination as a voltage divider with the relative resistance of exhaust gas sensor 24 and resistor 41 determining the fraction of voltage $V_c$ across exhaust gas sensor 24. Voltage $V_c$ can be obtained from any convenient source such as, for example, an automobile battery. A resistor 42 acts as an input resistor to couple sensing lead 28 to the negative input of an operational amplifier or comparator 43. The positive input to operational amplifier 43 is connected to a junction between resistors 44 and 45, which are connected between voltage $V_c$ and ground, thus establishing the reference voltage. A resistor 46 is connected between the output of operational amplifier 43 and the negative input terminal thus providing a feedback path which tends to stabilize operation. A resistor 47 is connected in series between the output of operational amplifier 43 and the positive input of comparator 70. A resistor 48 is connected between the positive input of comparator 70 and ground. Resistors 47 and 48 tend to act as a voltage divider for the output of operational amplifier 43 with respect to the positive input of comparator 70.

Compensation circuit 50 includes summing amplifier 51 having an output connected to the negative input of comparator 70 by conductive lead 72. The positive input of summing amplifier 51 is connected to the output of an operational amplifier or comparator 52 by a resistor 53 and to the output of an operational amplifier or comparator 54 by a resistor 55. The negative input of summing amplifier 51 is connected to ground through a resistor 56 and to the output of summing amplifier 51 by a variable resistor 57 thus varying amplification and permitting adjustment of the output of summing amplifier 51 with respect to the input of summing amplifier 51. The positive of input of operational amplifier 52 is connected to the curser of a variable resistance 58 which in turn is connected between ground and $V_c$ thus providing a bias voltage for the positive input of operational amplifier 52. The negative input of operational amplifier 52 is connected to the output of operational amplifier 52 to provide a stabilizing feedback. Analogously, the negative input of operational amplifier 54 is connected to the output of operational amplifier 54. The positive input of operational amplifier 54 is connected by conductive lead 32 to engine tachometer 31 and thus provides a buffer for the tachometer voltage.

Examples of particular values for elements in electronic circuit are:

$V_{cc} = 15$ volts D.C.

resistor 53 = 100 k Ω
resistor 55 = 100 k Ω
resistor 57 = 500 k Ω
resistor 56 = 47 k Ω
resistor 58 = 100 k Ω
comparator 70 = LM 339 National Semiconductor comparators or operational amplifiers
43, 52, 54 = LM 324 National Semiconductor

OPERATION

Electronic control means 26 compensates for the temperature dependence of titania exhaust gas sensor 24. That is, compensation of the variation in exhaust sensor 24 characteristics with temperature is done by engine speed dependent programming of the sensor's operating point. In brief, the exhaust sensor 24 operates as a stoichiometric exhaust air/fuel sensor. Ideally, the sensors is assumed to undergo a step change in some electrical characteristics, independent of temperature, as the exhaust air to fuel ratio changes through stoichiometry. The sensor signal is continually compared to a reference value which represents the sensor characteristics corresponding to the exhaust air to fuel ratio changing through the exact stoichiometric fuel value. An error signal is generated from this comparison to signal a need for correction to be made at the engine intake, for example, the carburetor.

In the case of a titania sensor such as exhaust gas sensor 24, a change in the exhaust air to fuel ratio through the stoichiometric value produces an abrupt change in the sensor's electrical resistance. Exhaust gas sensor 24 behaves as a variable resistance in the presence of hot gases having varying oxygen pressure so that the voltage across gas sensor 24 will be indicative of the instantaneous oxygen partial pressure. By communicating the voltage at sensor 24 to the electronic control circuit, a command signal may be generated for application by conductor 36 to air/fuel ratio modulator means to maintain the combustible mixture provided to engine 10 at a preselected, for example, stoichiometric air/fuel ratio. The value of resistance corresponding to the exact stoichiometric air to fuel ratio value is also a function of the exhaust gas temperature. To compensate for this dependence, a variable reference which is proportional to engine speed is used since a linear relationship has been found to exist between vehicle speed and the exhaust temperature. The circuit to implement this concept is shown in FIG. 2.

Generally, interface circuit 40 converts the resistance change of exhaust gas sensor 24 to a voltage. Further, interface circuit 40 acts as a buffer and generally provides an output voltage level which is compatible with the voltage operation level of comparator 70. That is, the two inputs to operational amplifier 43 are at an appropriate level to establish a difference voltage which has an appropriate magnitude for multiplication by operational amplifier 43. An output resistance divider including resistors 47 and 48 establishes an appropriate voltage level for the input of comparator 70.

In an analageous manner, compensation circuit 50 acts to provide a difference voltage with respect to the tachometer voltage which is an appropriate level for being an input to summing amplifier 51. Compensation circuit 50 sums the tachometer voltage available on conductive lead 32 with a bias voltage available at bias resistor 58 to yield a variable reference voltage available at the output of summing amplifier 51. Operational amplifier 54 acts as a buffer amplifier for the input of the tachometer voltage. Similarly, operational amplifier 52 acts as an operational buffer amplifier for the offset provided by the bias voltage. The output of operational amplifier 52 and 54 are coupled to resistors of equal magnitude to the positive input of summing amplifier 51. Then, this input is amplified by a desired gain to get the desired output voltage. The amplification is accomplished by the adjustment of variable resistor 57 in combination with resistor 56. The output of summing amplifier 51 is applied to the negative input of comparator 70 and provides a set point which is adjusted with respect to the voltage output of the titania sensor so that the output which is due to temperature is compensated. The gain of summing amplifier 51 and the bias voltage are determined from experimental data of exhaust gas sensor 24 electrical resistance versus the air to fuel ratio as a function of temperature. It has been shown on one test vehicle that the variable reference gives good results with only a 0.08 air to fuel ratio spread from idle to 60 mph while a fixed reference gives a 0.29 air to fuel ratio spread over the same speed range. Thus when the air fuel ratio is at a stoichiometric setting, the voltage output of the titania sensor is due to the temperature of the exhaust gases and is balanced by the temperature compensated output of the compensation circuit and the output of comparator 70 is a signal indicating no change in the air fuel ratio is necessary.

Various modifications and variations will no doubt occur to those skilled in the various arts to which this invention pertains. For example, a particular means for generating a bias voltage or given a difference between voltages may be varied from the apparatus disclosed herein. These and all other variations which basically rely on the teachings through which this disclosure has advanced the art are properly considered within the scope of this invention.

I claim:

1. A gas sensor construction coupled to an engine producing a gas stream comprising:
    a variably resistive gas and temperature responsive sensing element in communication with the gas stream for producing a first electrical signal responsive to the partial pressure of oxygen of the gas stream and to the temperature of the gas stream;
    a measuring means for developing a second electrical signal as a function of engine speed; and
    an electrical circuit means for processing the electrical signals from said sensing element and said measuring means so that said second electrical signal is used to reduce any temperature dependence in said first electrical signal.

2. A gas sensor construction as recited in claim 1 wherein:
    said electrical circuit means includes a bias voltage generating means for producing an output bias voltage, a summing amplifier means for combining said output bias voltage and said second electrical signal, said summing amplifier means having sufficient gain so that the combination of said output biase voltage and said second electrical signal is amplified to a magnitude which is sufficient to compensate for temperature dependence in said first electrical signal and has the general form of A (B+X), wherein A is the magnitude of the gain of said summing amplifier means, B is the magnitude of the bias voltage, and X is the magnitude of said second electrical signal.

3. A gas sensor construction as recited in claim 2 wherein:
said summing amplifier means is an operational amplifier with a positive input for receiving said output bias voltage and said second electrical signal and a negative input coupled through a variable resistor to the output of said summing amplifier means to adjust the amplification of the sum of said output bias voltage and said second electrical signal.

4. A gas sensor construction as recited in claim 1 wherein:
said sensing element has an electrical resistance which varies with the partial pressure of oxygen of the gas stream and with the temperature of the gas stream; and
said electrical circuit means is adapted to respond to a voltage drop across said sensing element, said voltage drop being a function of the magnitude of said electrical resistance of said sensing element.

5. A gas sensor construction as recited in claim 4 wherein:
said electrical circuit means includes a first comparator having a first input adapted to receive a signal which is a function of said first electrical signal and a second input adapted to receive a signal which is a function of said second electrical signal, said first comparator having a first output adapted to provide a signal which is a function of the partial pressure of oxygen and is compensated for temperature of the gas stream.

6. A gas sensor construction as recited in claim 5 wherein said electrical circuit means further includes:
a second comparator having a third input adapted to receive a signal which is a function of said first electrical signal, a fourth input adapted to receive a signal which is a function of a reference voltage, and a second output adapted to provide a signal which is a function of the difference between the reference voltage and said first electrical signal and coupled to said first input of said first comparator, said second comparator further comprising a first feedback means for applying the signal provided by said second output to said third input;
a third comparator having a fifth input adapted to receive a signal which is a function of engine speed, a sixth input adapted to receive a signal which has an adjustable voltage level, a third output coupled to said second input, and a second feedback means coupling said third output and said sixth input and including a means for varying the magnitude of the input voltage applied to said sixth input;
a fourth comparator having a fourth output coupled to said fifth input, a seventh input coupled to said fourth output and an eighth input coupled to a voltage biasing means, and
a fifth comparator having a fifth output coupled to said fifth input, a nineth input coupled to said fifth output and a tenth input adapted to receive an electrical signal changing in magnitude as a function of engine speed.

7. A system for temperature compensating the resistance variation of an engine exhaust gas sensor responsive to a partial pressure of oxygen indicative of the air/fuel ratio of engine operation comprising:

an interface means for establishing a first difference voltage which is a function of a reference voltage and a function of a sensor voltage which is related to the resistance of said exhaust gas sensor;
a compensation means for establishing a second difference voltage which is a function of a tachometer voltage related to engine speed and a function of a bias voltage which serves to adjust the magnitude of said second difference voltage; and
a first comparator means for establishing a third difference voltage which is a function of said first and second difference voltages and adapted to provide a first output for use in controlling the air/fuel ratio of engine operation, said first difference voltage being coupled to a first input and a second difference voltage being coupled to a second input.

8. A system for temperature compensating as recited in claim 7 wherein:
said interface means includes a second comparator having a second output, a third input coupled to said sensor voltage, a fourth input being coupled to said reference voltage and a first feedback means coupling said second output and said third input for stabilizing the electrical signal provided by said second output.

9. A system for temperature compensating as recited in claim 7 wherein said compensation means includes:
a third comparator having a fifth input coupled to a fourth output of a fourth comparator and a fifth output of a fifth comparator, said third comparator having a sixth input and a third output coupled by a second feedback means for adjusting the magnitude of the signal carried by said third output;
said fourth comparator having a seventh input coupled to said fourth output and an eighth input coupled to said sensor voltage; and
said fifth comparator having a nineth input coupled to said fifth output and a tenth input coupled to said tachometer voltage.

10. A system for temperature compensating as recited in claim 9 wherein:
said second feedback means includes a first resistor coupling said sixth input to ground and a second resistor coupling said third output to said sixth input, said second resistor being adjustable in magnitude so that the amplification gain at said third comparator means can be adjusted.

11. A system for temperature compensating as recited in claim 10 wherein:
said eighth input is coupled to a third resistor, said third resistor being adjustable so as to adjust the magnitude of the input voltage as said eighth input.

12. A system for temperature compensating as recited in claim 9 wherein:
said compensation means provides an output of the form A (B+X) where A is an amplification factor provided by said third comparator and said second feedback means, B is a function of the bias voltage and X is a function of the tachometer voltage.

13. A method for temperature compensating a gas sensing element including the step of:
developing a first signal dependent upon the temperature and partial pressure of oxygen of an exhaust gas stream produced by an engine;
generating a second signal dependent upon the speed of the engine; and
combining the first and second signals so that a third signal is generated which is substantially independent of the effect of the temperature of the gas stream and substantially dependent upon the partial pressure of oxygen of the gas stream.

14. A method as recited in claim 13 wherein generating said second signal dependent includes having the signal magnitude obey the equation A (B+X) where A is an amplification constant, B is a biasing constant and X is a function of the engine speed.

15. A method as recited in claim 14 wherein generating said second signal includes:
utilizing the voltage drop across a variable resistance to obtain the biasing constant B;
applying signals representing B and X to the input of summing amplifier; and
utilizing a variable resistance coupled between the output and input of the summing amplifier to obtain the constant A.

* * * * *